US011173271B2

(12) United States Patent
Glenn et al.

(10) Patent No.: US 11,173,271 B2
(45) Date of Patent: Nov. 16, 2021

(54) OXYGEN SENSOR ASSEMBLY FOR MEDICAL VENTILATOR

(71) Applicant: Covidien LP, Mansfield, MA (US)

(72) Inventors: Gregory J. Glenn, Irvine, CA (US); Jose J. Aguirre, Oceanside, CA (US); Matthew Tyson Grant, San Marcos, CA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 16/806,263

(22) Filed: Mar. 2, 2020

(65) Prior Publication Data

US 2020/0197651 A1    Jun. 25, 2020

Related U.S. Application Data

(62) Division of application No. 15/058,024, filed on Mar. 1, 2016, now Pat. No. 10,596,343.

(Continued)

(51) Int. Cl.
*A61M 16/10* (2006.01)
*A61M 16/08* (2006.01)
(Continued)

(52) U.S. Cl.
CPC .... *A61M 16/1005* (2014.02); *A61M 16/0003* (2014.02); *A61M 16/0051* (2013.01);
(Continued)

(58) Field of Classification Search
CPC .......... A61M 16/0051; A61M 16/1005; A61M 16/0816; A61M 16/20; A61M 16/0833; A61B 5/082; A61B 5/0833; A61B 5/0873
See application file for complete search history.

(56) References Cited

U.S. PATENT DOCUMENTS 4,677,976 A    7/1987 Fujinuma
7,814,907 B2 *  10/2010 Bremner ............. A61M 16/109
                                         128/205.23
(Continued)

FOREIGN PATENT DOCUMENTS

| CN | 103893892 | 7/2014 |
| WO | 20130064183 | 5/2013 |
| WO | 20140184377 | 11/2014 |

OTHER PUBLICATIONS

Notification of Transmittal of the International Search Report and the PCT Written Opinion of the International Searching Authority, or the Declaration, dated May 3, 2016, International application No. PCT/US2016/02087 International Filing date Mar. 1, 2016, Applicant Covidien LP.

(Continued)

*Primary Examiner* — Samchuan C Yao
*Assistant Examiner* — Cana A Gallegos

(57) ABSTRACT

The present invention relates to oxygen sensors for medical ventilators. A medical ventilator includes a patient circuit delivering inspiratory airflow to a patient and returning expiratory airflow from the patient back to the ventilator. A manifold includes an air flow path into the patient circuit, and a port with an opening for an oxygen sensor. When mated to the port, the oxygen sensor samples the air in the air flow path and detects the amount of oxygen in the air. When the oxygen sensor is inserted into the port, a valve is biased open, to allow airflow through the opening into the oxygen sensor during ventilation. When the oxygen sensor is removed from the port, the valve biases into a closed position covering the opening, to prevent leaks. The ventilator can then continue to operate without the oxygen sensor in place.

13 Claims, 7 Drawing Sheets

Related U.S. Application Data

(60) Provisional application No. 62/126,923, filed on Mar. 2, 2015.

(51) Int. Cl.
*A61M 16/20* (2006.01)
*A61M 16/00* (2006.01)

(52) U.S. Cl.
CPC ...... *A61M 16/0057* (2013.01); *A61M 16/024* (2017.08); *A61M 16/0816* (2013.01); *A61M 16/0833* (2014.02); *A61M 16/20* (2013.01); *A61M 16/201* (2014.02); *A61M 16/0063* (2014.02); *A61M 2016/1025* (2013.01); *A61M 2205/3317* (2013.01)

(56) References Cited

U.S. PATENT DOCUMENTS

| | | | |
|---|---|---|---|
| 8,844,526 B2 | 9/2014 | Jafari et al. |
| 8,905,024 B2 | 12/2014 | Jafari et al. |
| 8,939,150 B2 | 1/2015 | Jourdain et al. |
| 8,950,398 B2 | 2/2015 | Andrieux et al. |
| 8,973,577 B2 | 3/2015 | Jafari et al. |
| 8,978,650 B2 | 3/2015 | Jafari et al. |
| 9,022,031 B2 | 5/2015 | Nakai et al. |
| 9,027,552 B2 | 5/2015 | Angelico et al. |
| 9,030,304 B2 | 5/2015 | Milne et al. |
| 9,089,657 B2 | 7/2015 | Kimm et al. |
| 9,089,665 B2 | 7/2015 | Patel |
| 9,114,220 B2 | 8/2015 | Masic |
| 9,126,001 B2 | 9/2015 | Masic et al. |
| 9,144,658 B2 | 9/2015 | Li et al. |
| 9,205,221 B2 | 12/2015 | Winter et al. |
| 9,254,369 B2 | 2/2016 | Jourdain et al. |
| 9,262,588 B2 | 2/2016 | Skidmore |
| 9,289,573 B2 | 3/2016 | Platt et al. |
| 9,327,089 B2 | 5/2016 | Jafari et al. |
| 9,358,355 B2 | 6/2016 | Graboi et al. |
| 9,364,624 B2 | 6/2016 | Jafari et al. |
| 9,364,626 B2 | 6/2016 | Carter et al. |
| 9,375,542 B2 | 6/2016 | Doyle et al. |
| 9,411,494 B2 | 8/2016 | Baker, Jr. |
| 9,414,769 B2 | 8/2016 | Karst et al. |
| 9,421,338 B2 | 8/2016 | Jafari et al. |
| 9,492,629 B2 | 11/2016 | Sanchez et al. |
| 9,498,589 B2 | 11/2016 | Jafari et al. |
| 9,675,771 B2 | 6/2017 | Jafari et al. |
| 9,808,591 B2 | 11/2017 | Esmaeil-zadeh-azar |
| 9,820,681 B2 | 11/2017 | Baker, Jr. |
| 9,925,345 B2 | 3/2018 | Masic |
| 9,950,135 B2 | 4/2018 | Winter |
| 9,956,363 B2 | 5/2018 | Masic |
| 9,981,096 B2 | 5/2018 | Sanchez et al. |
| 9,993,604 B2 | 6/2018 | Doyle et al. |
| 10,064,583 B2 | 9/2018 | Nakai et al. |
| 10,362,967 B2 | 7/2019 | Milne et al. |
| 10,596,343 B2 | 3/2020 | Glenn |
| 2009/0212962 A1* | 8/2009 | Chekal ................ A62B 18/088 340/632 |
| 2010/0168599 A1 | 7/2010 | Esposito |
| 2011/0155132 A1 | 6/2011 | Virr |
| 2012/0085435 A1* | 4/2012 | Feng .................... A61M 16/20 137/467.5 |
| 2013/0074844 A1 | 3/2013 | Kimm et al. |
| 2013/0081536 A1 | 4/2013 | Crawford, Jr. et al. |
| 2013/0158370 A1 | 6/2013 | Doyle et al. |
| 2013/0167843 A1 | 7/2013 | Kimm et al. |
| 2013/0220324 A1 | 8/2013 | Jafar et al. |
| 2013/0239038 A1 | 9/2013 | Skidmore et al. |
| 2013/0327331 A1 | 12/2013 | Bourdon |
| 2013/0333703 A1 | 12/2013 | Wallace et al. |
| 2013/0345532 A1 | 12/2013 | Doyle et al. |
| 2014/0000606 A1 | 1/2014 | Doyle et al. |
| 2014/0048071 A1 | 2/2014 | Milne et al. |
| 2014/0048072 A1 | 2/2014 | Angelico et al. |
| 2014/0052014 A1* | 2/2014 | Jaffe ...................... A61B 5/742 600/532 |
| 2014/0130798 A1 | 5/2014 | Milne et al. |
| 2014/0261409 A1 | 9/2014 | Dong et al. |
| 2014/0261424 A1 | 9/2014 | Doyle et al. |
| 2014/0290657 A1 | 10/2014 | Vandine et al. |
| 2014/0326048 A1 | 11/2014 | Jaffe |
| 2014/0366879 A1 | 12/2014 | Kimm et al. |
| 2014/0373845 A1 | 12/2014 | Dong |
| 2015/0034082 A1 | 2/2015 | Kimm et al. |
| 2015/0090258 A1 | 4/2015 | Milne et al. |
| 2015/0090264 A1 | 4/2015 | Dong |
| 2015/0100917 A1 | 4/2015 | Palmer |
| 2015/0202394 A1 | 7/2015 | Angelico et al. |
| 2015/0224272 A1 | 8/2015 | Milne et al. |
| 2018/0028769 A1 | 2/2018 | Obenchain |
| 2018/0078752 A1 | 3/2018 | Gulliver |
| 2018/0177961 A1 | 6/2018 | Kagan |

OTHER PUBLICATIONS

7200 Series Ventilator, Options, and Accessories: Operator's Manual. Nellcor Puritan Bennett, Part No. 22300 A, Sep. 1990, pp. 1-196.
7200 Ventilatory System: Addendum/Errata. Nellcor Puritan Bennett, Part No. 4-023576-00, Rev. A, Apr. 1998, pp. 1-32.
800 Operator's and Technical Reference Manual Series Ventilator System, Nellcor Puritan Bennett, Part No. 4-070088-00, Rev. L, Aug. 2010, pp. 1-476.
840 Operator's and Technical Reference Manual Ventilator System, Nellcor Puritan Bennett, Part No. 4-075609-00, Rev. G, Oct. 2006, pp. 1-424.
Puritan Bennett 980 Series Ventilator Operator's Manual, Covidien, Jan. 29, 2014, Part. No. 10077893 A Jan. 2014, 506 pages.

* cited by examiner

OXYGEN SENSOR ASSEMBLY FOR MEDICAL VENTILATOR

CROSS-REFERENCE TO RELATED APPLICATIONS

This application is a divisional application of U.S. patent application Ser. No. 15/058,024, titled "OXYGEN SENSOR ASSEMBLY FOR MEDICAL VENTILATOR," filed on Mar. 1, 2016, which claims the benefit of U.S. Provisional Application Ser. No. 62/126,923, filed Mar. 2, 2015, the complete disclosures of which are hereby incorporated by reference in their entirety. To the extent appropriate, priority is claimed to both applications.

FIELD

The present invention relates to oxygen sensors for medical ventilators.

BACKGROUND

Medical ventilators can provide life-sustaining oxygen delivery to critically ill patients who may otherwise be unable to breathe sufficiently. Ventilators can mix oxygen with room air to achieve a desired percentage of oxygen in the air delivered to the patient. Some ventilators include an oxygen sensor that samples the flow of air being delivered to the patient and detects the amount of oxygen in the delivered air. The information from the oxygen sensor enables the ventilator to check that the oxygen delivery system is working appropriately, to confirm that the appropriate oxygen percentage is maintained, and/or to make adjustments if necessary.

The oxygen sensor may need to be periodically removed from the ventilator in order to be cleaned or replaced. In some cases, the ventilator is removed from service so that the oxygen sensor can be replaced while the ventilator is not operating on a patient.

SUMMARY

A medical ventilator includes a patient circuit delivering inspiratory airflow to a patient and returning expiratory airflow from the patient back to the ventilator. A manifold includes an air flow path into the patient circuit, and a port with an opening for an oxygen sensor. When mated to the port, the oxygen sensor samples the air in the air flow path and detects the amount of oxygen in the air. When the oxygen sensor is inserted into the port, a valve is biased open, to allow airflow through the opening into the oxygen sensor during ventilation. When the oxygen sensor is removed from the port, the valve biases into a closed position covering the opening, to prevent leaks. The ventilator can then continue to operate without the oxygen sensor in place.

In an embodiment, a medical ventilator includes a manifold with a first air flow path to a patient circuit. The ventilator also includes a port in the manifold. The port has a second air flow path through an opening in the port. The first and second air flow paths are in fluid communication with each other, and the port is configured to mate with an oxygen sensor assembly. The ventilator also includes a valve biased toward a closed position in which the valve closes the opening. The valve is movable, by insertion of the oxygen sensor assembly, into an open position in which the second air flow path through the opening is exposed.

In an embodiment, a method for replacing an oxygen sensor on a medical ventilator includes mating an oxygen sensor assembly to a port of a medical ventilator. The oxygen sensor assembly has an oxygen sensor, and the port includes a valve biased to close the port. The method also includes operating the medical ventilator with the oxygen sensor, and removing the oxygen sensor assembly from the port. Mating the oxygen sensor assembly to the port includes automatically opening the valve, and removing the oxygen sensor assembly from the port includes automatically closing the valve.

In an embodiment, an oxygen sensor assembly for a medical ventilator includes an adapter with a surface that interfaces with the medical ventilator to open a valve to allow airflow from the medical ventilator to the oxygen sensor. Optionally, the adapter includes a body and a latch. The body includes a cavity for receiving an oxygen sensor, and the latch is movable to retain the oxygen sensor assembly to the ventilator. The body includes either a groove or a projection, and the latch includes the other of the groove or the projection, such that the groove and the projection mate to secure the latch to the body. In an embodiment, the oxygen sensor assembly also includes an oxygen sensor.

DETAILED DESCRIPTION

The present invention relates to oxygen sensors for medical ventilators. In an embodiment, a medical ventilator includes a valve that closes when the oxygen sensor is removed from the ventilator, to allow the ventilator to continue to operate without air flow leaks when the oxygen sensor is removed.

In an embodiment, a medical ventilator includes a patient circuit delivering inspiratory airflow to a patient and returning expiratory airflow from the patient back to the ventilator. A manifold includes an air flow path into the patient circuit, and a port with an opening for an oxygen sensor. When mated to the port, the oxygen sensor samples the air in the air flow path and detects the amount of oxygen in the air. When the oxygen sensor is inserted into the port, a valve is biased open, to allow airflow through the opening into the oxygen sensor during ventilation. When the oxygen sensor is removed from the port, the valve biases into a closed position covering the opening, to prevent leaks. The ventilator can then continue to operate without the oxygen sensor in place. The valve may be positioned to open automatically when the sensor is mated to the port, and to close automatically when the sensor is removed. In an embodiment, the oxygen sensor is received into an adapter that is configured to interact with the valve to open the valve when the oxygen sensor is mated to the port. In an embodiment, the oxygen sensor and the adapter are integrated together.

Figure 1:
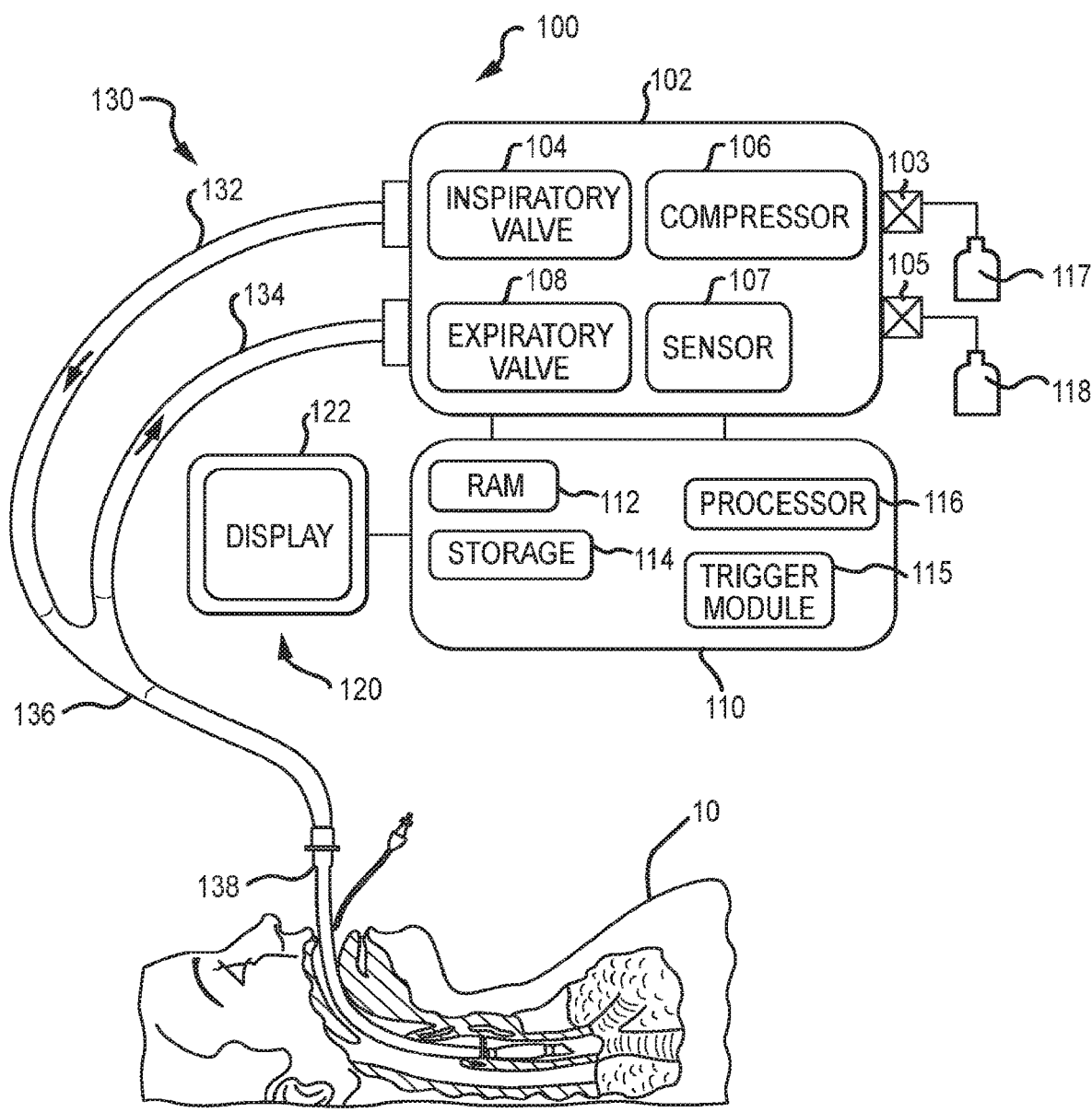
FIG. 1 illustrates a schematic view of a medical ventilator interacting with a human patient, according to an embodiment of the present disclosure.

FIG. 1 shows a schematic view of a ventilator 100 providing ventilation to a human patient 10, according to an embodiment. The ventilator 100 includes a pneumatic system 102 coupled to a patient circuit 130 that provides airflow between the ventilator and the patient. In an embodiment, the patient circuit 130 includes a set of tubes that connect at one end to the ventilator and at the other end to a patient interface 138. The patient interface 138 includes suitable tubing and seals for insertion into a patient's airway, or for use around the patient's nose and mouth. In an embodiment, the patient circuit 130 includes an inspiratory limb 132, delivering airflow from the ventilator to the patient, and an expiratory limb 134, delivering exhaled airflow from the patient to the ventilator. The two limbs may be joined at a wye fitting 136, leading to the patient interface 138. Airflow into the patient circuit 130 is controlled by the pneumatic system 102. Specifically, the pneumatic system includes an inspiratory valve 104 that controls airflow into the inspiratory limb 132, and an expiratory valve 108 that controls airflow exiting the expiratory limb 134.

In an embodiment, the pneumatic system 102 also includes a compressor 106, one or more sensors 107, such as pressure sensors, flow sensors, temperature sensors, gas sensors, and/or other sensors, and various valves, fittings, and conduits routing air flow to and from the inspiratory and expiratory valves. In some embodiments, the pneumatic system 102 includes pressure-regulating valves 103 and 105 that control pressurized air and oxygen sources 117 and 118, respectively. The pressurized air and oxygen sources may be available from wall outlets (in modern medical facilities) or from tanks. These air sources are represented as tanks in FIG. 1, but may be wall outlets or other sources. These pressure regulating valves (or regulators) 103 and 105 control the release of air and oxygen from these wall outlets or tanks. Each regulating valve regulates flow from its tank so that the combined respiratory gas delivered to the patient has a desired concentration of oxygen and is supplied to the patient at desired pressures and rates. In this context, an oxygen sensor is often included in order to sample the airflow to the patient and confirm that the appropriate oxygen concentration is being delivered.

Still referring to FIG. 1, the ventilator 100 also includes a user interface 120 including a display screen 122. In an embodiment, the display screen 122 is a touch screen that receives user inputs and a display that displays information. For example, the display 122 enables a user to view current patient parameters, change pressure and flow settings, adjust alarm limits, view historical data, and pause audible alarms, among other functions.

Still referring to FIG. 1, the ventilator 100 also includes a controller 110 that includes a processor 116, memory 112 such as random access memory (RAM), data storage 114, and/or other components commonly found in computing devices. The memory 112 may include non-transitory, computer-readable storage media that stores software that is executed by the processor 116 and which controls the operation of the ventilator 100. In an embodiment, the memory 112 includes one or more solid-state storage devices such as flash memory chips. In an alternative embodiment, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 116. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

In an embodiment, the controller 110 also includes a trigger module 115, which triggers inspiration according to ventilator settings, such as those prescribed by a clinician. In an embodiment, the trigger module 115 triggers an inspiration based on expiration of a determined amount of time (for the patient to exhale), or based on detection of a trigger condition (such as patient effort to breathe). In response to a trigger from the trigger module, the control system sends control signals to the pneumatic system 102 to operate the inspiratory and expiratory valves to deliver air to the patient.

Figure 2:
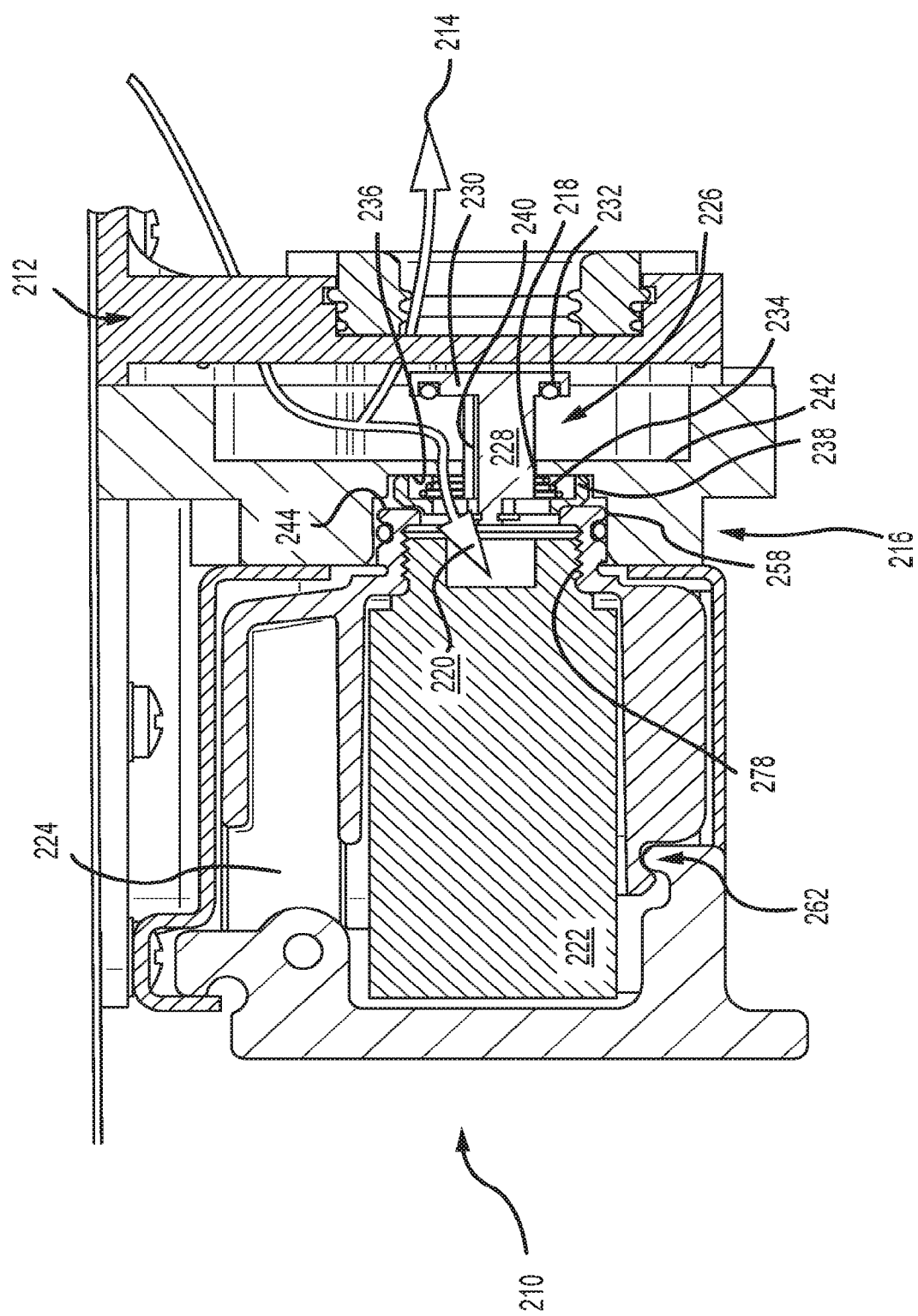
FIG. 2 illustrates a cross-sectional view of an oxygen sensor assembly mated to a port of a medical ventilator, according to an embodiment of the present disclosure.

FIG. 2 shows an oxygen sensor assembly 210 mated to a ventilator manifold 212, according to an embodiment of the invention. The manifold 212 includes a first air flow path 214 that conveys air flow to the patient circuit 130 (shown in FIG. 1). This air flow path 214 is downstream of the pressure regulating valves 103 and 105 (shown in FIG. 1), and includes mixed air and oxygen that will be delivered to the patient for breathing. The manifold 212 also includes a port 216 that mates with the oxygen sensor assembly 210. The port 216 includes a second air flow path 220 through an opening 218 in the port 216. This opening 218 allows air to flow through the port and into the oxygen sensor assembly, where the oxygen content of the air is measured. The two air flow paths 214 and 220 are in fluid communication with each other, such that same air flow that is delivered to the patient is sampled by the oxygen sensor.

The oxygen sensor assembly 210 includes an oxygen sensor 222 retained by a sensor adapter 224. The adapter 224 will be described in more detail below with reference to FIG. 4. The oxygen sensor 222 itself is a sensor that can measure the concentration of oxygen in a sample of air. The oxygen sensor may be a chemical sensor such as a galvanometric oxygen sensor. As another alternative, the oxygen sensor may be a magnetic sensor that operates based on the magnetic properties of oxygen. Other types of oxygen sensors that measure the concentration (such as a percentage) of oxygen within a sample or flow of air may be suitable for use with the ventilator 100.

Referring again to FIG. 2, a sensor shutoff valve 226 is positioned to interact with the port 216 to open and close the port when the oxygen sensor is inserted and removed from the port. The oxygen sensor assembly 210 interacts with the valve to open the valve when the oxygen sensor assembly is inserted into the port, and maintain the valve open while the oxygen sensor assembly is mated to the port. A biasing element or actuator operates to automatically close the valve when the oxygen sensor is removed from the port. In FIG. 2, the valve is shown in the open position. In the open position, the opening 218 is exposed to the air flow path 220, and thereby allowing air to flow through the opening 218 into the oxygen sensor 222.

The valve 226 that is shown in FIG. 2 will be described in more detail, though it will be understood that other types of valves may be suitable as well. In FIG. 2, the valve 226 includes a spring-biased valve with a movable plunger 228. The plunger 228 translates through the opening 218, toward and away from the manifold. In the embodiment shown, the biasing element or actuator includes a spring 234 that is trapped between an outward face 236 of the manifold and a retainer 238. The retainer 238 is retained to the plunger 228 by a suitable fastener which may be a separate piece, or integrated with the retainer. The retainer itself includes openings, passages, or perforations that allow passage of air flow through the retainer into the oxygen sensor. When the valve is open, the spring is compressed between the outward face 236 and the retainer 238, and the plunger 228 is translated into the manifold, away from the oxygen sensor 222. The shaft of the plunger includes a cross-sectional area that is smaller than the opening 218, thereby exposing a passage 240 between the plunger and the edges of the opening 218. When the oxygen sensor is removed, the spring expands, moving the plunger away from the manifold and toward the former position of the oxygen sensor, until a foot 230 at the end of the plunger reaches a seating surface 242 of the manifold. The foot 230 is larger than the opening 218. When the foot 230 is seated against the seating surface 242, the foot covers the opening, closing the air flow path 220. The foot may include a gasket or seal 232, such as an o-ring, to prevent air from leaking out of the manifold between the foot and the seating surface 242. Additionally, the spring urges the foot against the seating surface to contribute to a tight seal.

When the oxygen sensor assembly is inserted again into the port 216, a front face 244 of the sensor adapter 224 makes contact with the retainer and pushes the retainer toward the manifold. This movement compresses the spring 234 and moves the foot 230 away from the seating surface 242, thereby exposing the passage 240 through the opening 218. A portion of the air flowing through the first flow path 214 to the patient interface flows through the passage into the oxygen sensor for measurement. While FIG. 2 shows the front face 244 of the sensor adapter 224 making this contact, in other embodiments, the oxygen sensor 222 itself can interact with the valve to open the valve, without the use of a sensor adapter. For example, the oxygen sensor may be push-fit, snapped, threaded, or otherwise mated directly into the port 216, without a sensor adapter between the sensor and the port. In this case, a front face or other feature on the oxygen sensor itself can contact the valve 226 to open the valve when the sensor is inserted into the port, or the oxygen sensor can trigger an actuator that opens the valve, as described further below.

Figure 3A:
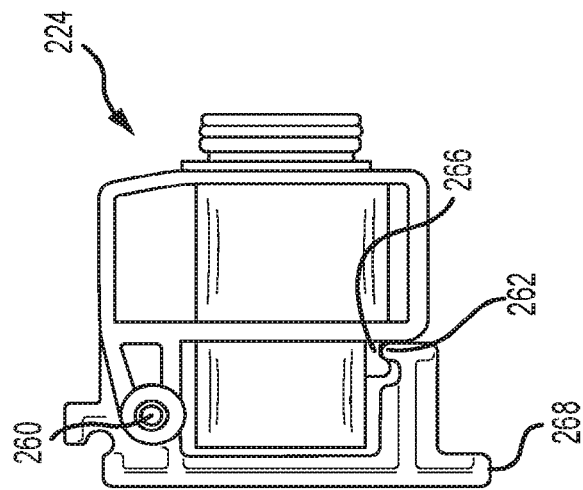
FIGS. 3A-B illustrate side views of an oxygen sensor assembly in open and closed positions, respectively, according to an embodiment of the present disclosure.
Figure 3B:
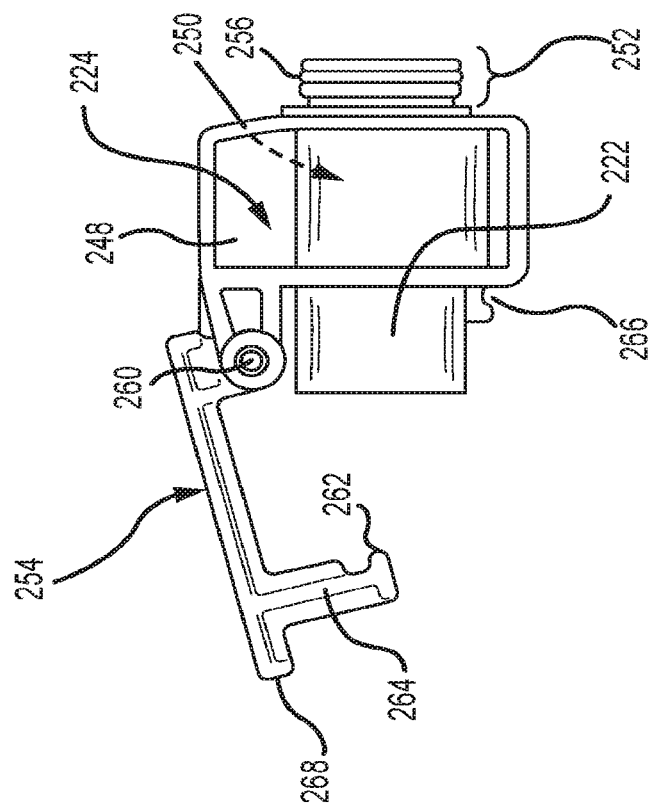

Two perspective views of the oxygen sensor assembly 210 are shown in FIGS. 3A and 3B, to illustrate the latching features of the adapter 224. The adapter 224 includes a body 248 that forms a cavity 250 that receives the front end of the oxygen sensor 222. In an embodiment, the oxygen sensor includes threads that mate with threads inside the cavity 250 (see threads 278 in FIGS. 2 and 4A-C) to retain the oxygen sensor to the adapter. These threads are optional; in other cases, the oxygen sensor may be retained to the adapter by a slip or friction fit, or by a latch such as the latch 254 (described more below). The adapter 224 includes a plug 252 at a first end of the adapter, and a latch 254 at a second, opposite end. The plug 252 contacts the valve in the manifold to open the valve when the sensor assembly is inserted into the ventilator (as described with reference to FIG. 2). The plug 252 also includes a seal 256 such as a gasket or o-ring that contacts a sealing surface 258 of the port 216 (see FIG. 2) to prevent air from leaking out of the ventilator between the manifold and the sensor assembly when the sensor assembly is mated to the port. The spring 234 can be chosen such that it is not strong enough to push the oxygen sensor assembly out of the port against the friction of the o-ring 256. In another embodiment, the plug 252 includes threads (not shown) that engage mating threads on the port to secure the adapter to the port, or other mechanical mating features.

The latch 254 rotates about a hinge 260 between open and closed positions. In an embodiment, the latch 254 rotates freely, without being biased or urged into either position. The latch includes a foot 264 opposite the hinge 260. The foot includes a detent or projection 262 that engages a matching groove 266 on the adapter opposite the hinge. In FIG. 3A, the latch is shown rotated outwardly away from the groove or indentation 266, toward the open position in which the oxygen sensor 222 can be slid out from the cavity 250 and removed from the adapter 224. In FIG. 3B, the latch is rotated toward the adapter, and the detent 262 is mated with the groove 266. The engagement of the detent with the groove secures the latch in place behind the oxygen sensor, opposite the plug 252. It should be noted that the figures show a detent 262 on the latch and a groove 266 on the adapter, but these may be reversed, or other suitable mating features may be used.

The latch 254 also includes a grip 268 opposite the hinge 260. To remove the oxygen sensor from the sensor adapter, a user can push against the grip 268, which will cause the latch detent 262 to disengage from the groove 266 as the latch rotates about the hinge 260, as described more fully below with references to FIGS. 4A-C.

Figure 4A:
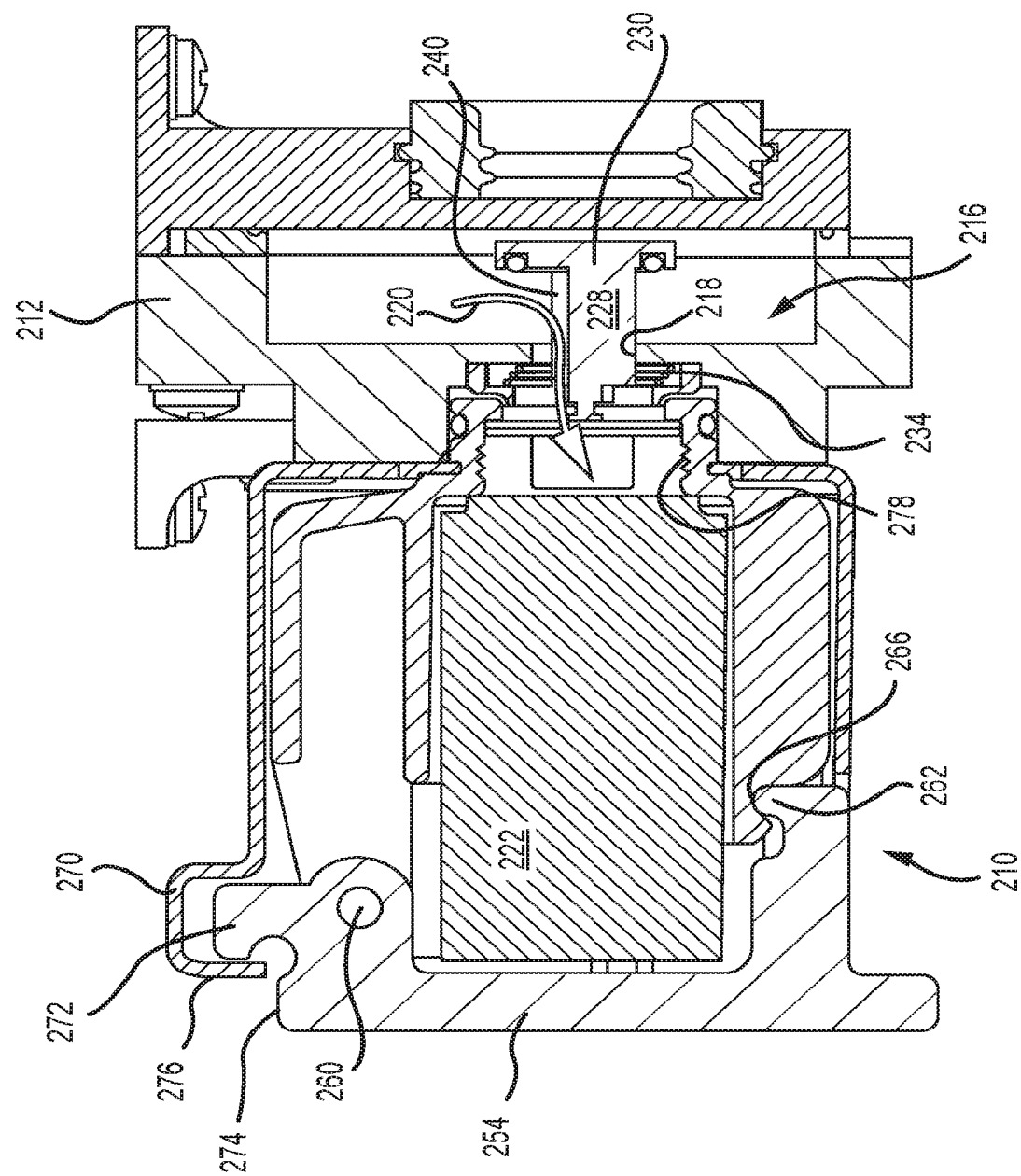
FIGS. 4A-C illustrate cross-sectional views of the oxygen sensor assembly and port of FIG. 2, in stages of insertion and removal.
Figure 4B:
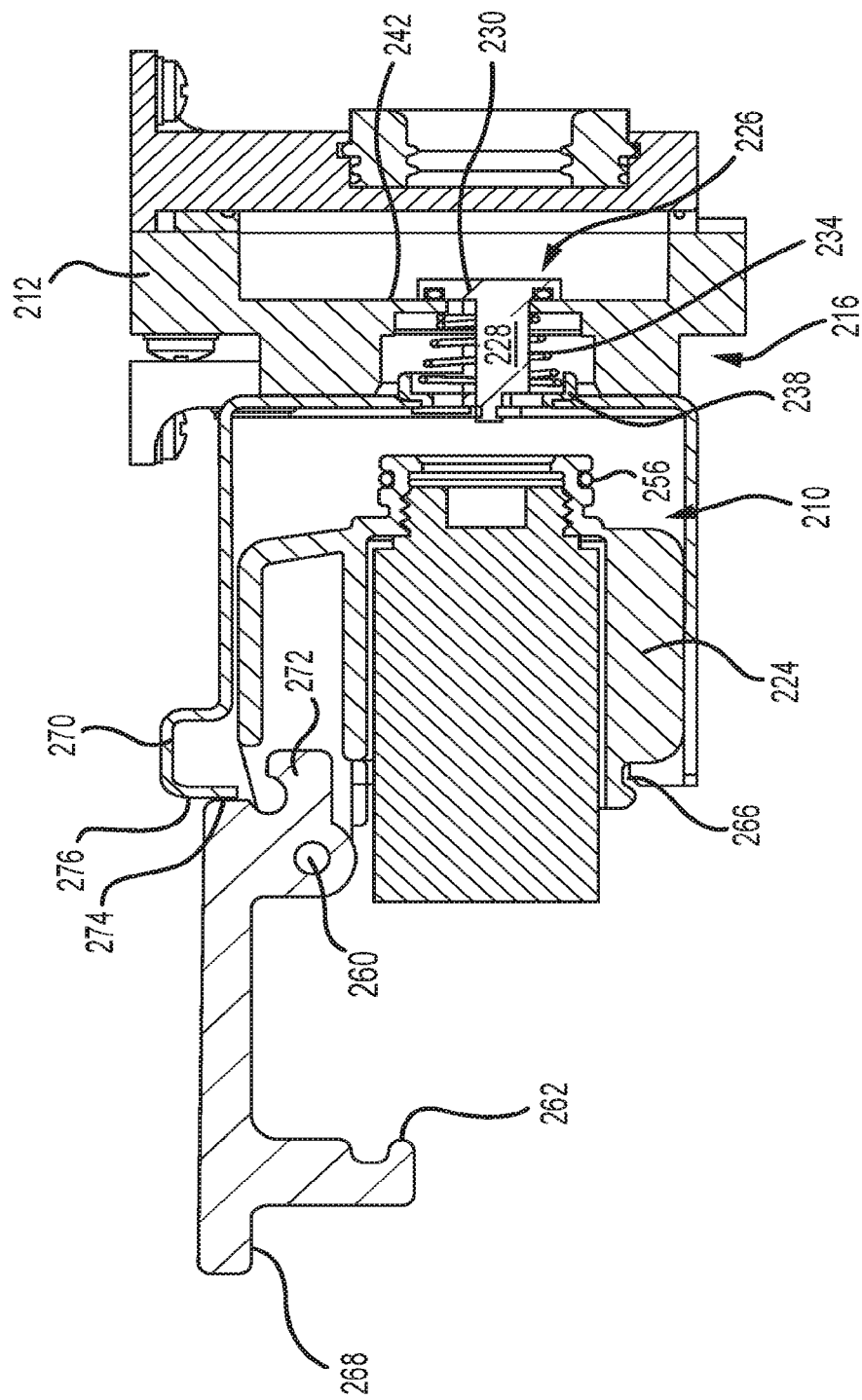
Figure 4C:
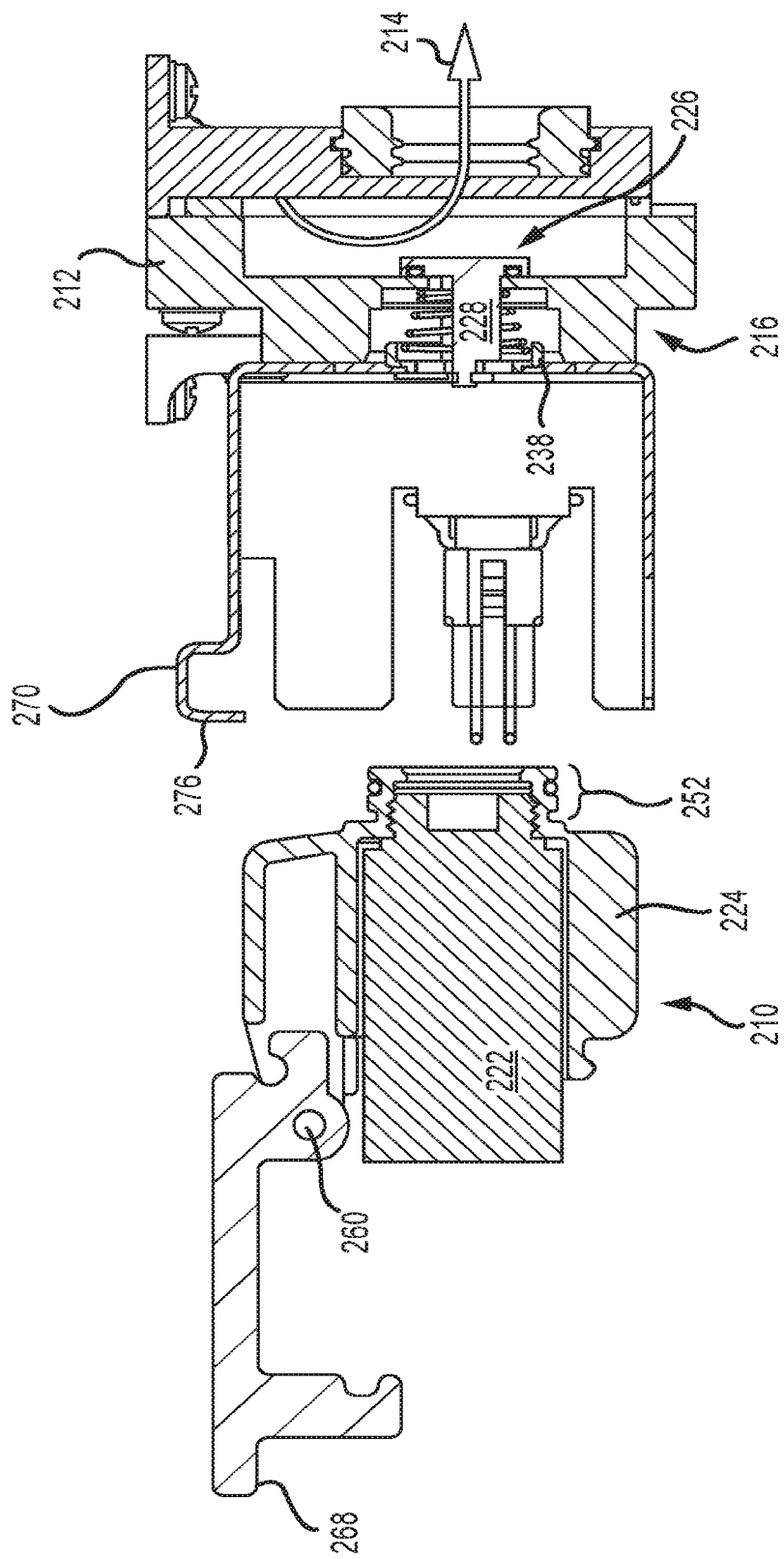

FIGS. 4A-C show the oxygen sensor assembly 210 in three stages of insertion/removal from the ventilator manifold 212. In FIG. 4A, the oxygen sensor assembly 210 is fully mated to the port 216, and the second air flow path 220 through the passage 240 into the oxygen sensor 222 is open. The spring 234 of the valve is compressed, and the foot 230 of the plunger 228 is pushed away from the opening 218. The latch 254 of the sensor adapter is in the closed position, with the detent 262 engaging the groove 266. As described below and with reference to these Figures, the latch 254 assists in retaining the oxygen sensor assembly to the ventilator port.

Additionally, in the embodiment shown, the manifold 212 includes a clip or trap 270 that engages a wing 272 of the latch 254. The wing 272 rotates about the hinge 260 with the latch 254. When the oxygen sensor is fully mated to the port 216, the latch 254 is closed, and the wing 272 is seated in the clip 270. The clip 270 holds the latch in place, preventing the spring 234 of the valve from pushing the oxygen sensor out away from the port 216. Optionally, an additional rear door (not shown) can be closed behind the latch, further securing the oxygen sensor into the port. Such a door also confirms to the user that the oxygen sensor has been installed to the correct depth in the port, as the door can be positioned such that it cannot close if the oxygen sensor is not fully seated into the port.

FIG. 4B shows the oxygen sensor assembly in a first stage of release from the port 216. To release the oxygen sensor from the port, the latch is rotated outwardly away from the manifold. The user pushes the grip 268 to release the detent 262 from the groove 266 and free the latch to rotate. As the latch rotates about the hinge 260, the wing 272 rotates down and out of the clip 270. As the latch further rotates, an end surface 274 of the latch abuts an end surface 276 of the clip 270. The contact between these two surfaces prevents the end surface 274 from further rotating with respect to the hinge. As a result, as the user continues to pull on the grip 268 to rotate the latch, the sensor adapter slides out from the port 216. The latch acts as a lever, with the end surface 274 pressing against the clip end surface 276 to provide leverage to move the sensor out of the port. The asymmetry of the latch about the hinge 260 forms a lever arm that translates a smaller force applied by the user about the hinge into a larger force applied against the surface 276. This leverage can be useful in case the seal or o-ring 256 on the sensor adapter sticks to the manifold, which can happen over time.

In an embodiment, a small amount of force applied by the user to the grip 268, such as 2 pounds, is translated by the latch into a larger resulting amount of force, such as 10 pounds, applied by the end surface 274 of the latch against surface 276 of the clip 270. In an embodiment, the lever arm amplification is about 3:1, or 4:1, or 5:1. In an embodiment, the force required to push the latch 254 closed (pushing the detent 262 into the groove 266) is about 2 pounds.

The interaction of the wing 272 and clip 270 also assists the user in positioning the oxygen sensor assembly 210 to the correct depth within the port 216, and gives a tactile feedback indicating that the oxygen sensor has been correctly installed. The engagement of the detent 262 into the groove 266 also provides a tactile and optionally audible "click" that confirms that the latch is in the proper position.

As the sensor assembly 210 moves away from the port 216, the valve 226 automatically moves into the closed position. As shown in FIG. 4B, the spring 234 expands, pushing against the retainer 238 and causing the plunger 228 to move outwardly away from the manifold, toward the oxygen sensor, until the foot 230 of the plunger rests against the seating surface 242.

FIG. 4C shows the oxygen sensor assembly 210 fully removed from the port 216, and the valve 226 fully closed. In this position, the foot of the plunger of the valve provides a seal against the seating surface of the manifold, preventing airflow from escaping through the opening 218. Airflow continues through the first air flow path 214 to the patient circuit, without loss of air through the oxygen sensor port 216. The oxygen sensor 222 may be removed from the adapter and either cleaned or discarded, and a new or cleaned sensor may be replaced.

As shown in FIGS. 4B and 4C, in an embodiment, the valve 226 automatically opens when the oxygen sensor is inserted, and automatically closes when the oxygen sensor is removed. The user can simply press the grip 268 to remove the oxygen sensor assembly 210, without introducing a large leak into the patient breath circuit through the opening 218. The valve is automatically biased to close the opening 218 when the oxygen sensor is removed, so that the port 216 is sealed. The ventilator can then continue to provide accurate breaths to ventilate the patient, albeit without the confirming measurement of oxygen concentration provided by the oxygen sensor. If the oxygen sensor is simply being quickly cleaned and/or replaced, the ventilator can continue to operate safely without the oxygen sensor for a short period of time. Then the new and/or cleaned oxygen sensor can be inserted into the port 216 when ready, and the oxygen sensor can again provide measurements of oxygen concentration to verify that the correct concentration is being provided to the patient. Throughout this process, the ventilator does not need to be taken out of service, and the patient does not need to be moved to a new ventilator in order to remove or replace the oxygen sensor. Additionally, the interactions of the latch and the manifold make it easy for the user to confirm that the oxygen sensor is fully mated to the port.

In an embodiment, a ventilator such as ventilator 100 (shown in FIG. 1) includes a user interface such as user interface 120 that interacts with the user regarding the presence, function, and/or removal of the oxygen sensor. In an embodiment, the ventilator includes a sensor or switch that detects when the oxygen sensor is not connected to the port 216. The switch can be a physical switch contacted by the oxygen sensor (or sensor assembly), an optical gate blocked by the oxygen sensor, an electrical contact made by the oxygen sensor, a position sensor that detects opening of a component such as the latch or access door behind the oxygen sensor, a magnetic sensor, or any other suitable switch or sensor. This switch may inform the ventilator that the oxygen sensor is removed or about to be removed, or that it is not properly or fully seated in the port. In an embodiment, such a switch may trigger an actuator that operates the valve. In this case, insertion of the sensor (or sensor assembly) activates the switch, when then triggers the actuator to open the valve, and removal of the sensor similarly triggers the actuator to close the valve. In this way, insertion and removal of the oxygen sensor can control the valve without requiring physical contact between the sensor and the valve.

When the ventilator detects that the oxygen sensor is not installed, the ventilator displays a warning and/or notification through the display 122 of the user interface 120. The warning may include visual and/or audible alerts, such as a written message, flashing colors, and audible sounds. The user interface 120 also includes an input (such as a touchscreen, interactive menu, buttons, keys, etc.) that enables the user to disable these alarms or warnings, or put them on a temporary pause. The user can then replace or clean the oxygen sensor while the ventilator continues to ventilate the patient. In an embodiment, the user interface includes an input or menu or other mechanism for the user to inform the ventilator, prior to removing the oxygen sensor, that the user is about to remove the oxygen sensor for replacement or cleaning. The user inputs this information through the user interface, and then the ventilator enters a mode of operation in which it does not rely on or attempt to use the measurement from the oxygen sensor. In this mode, when the user removes the oxygen sensor, the ventilator does not produce an alarm. The ventilator may still provide a written warning or message or other display that indicates that it is operating without an oxygen sensor.

Figure 5:
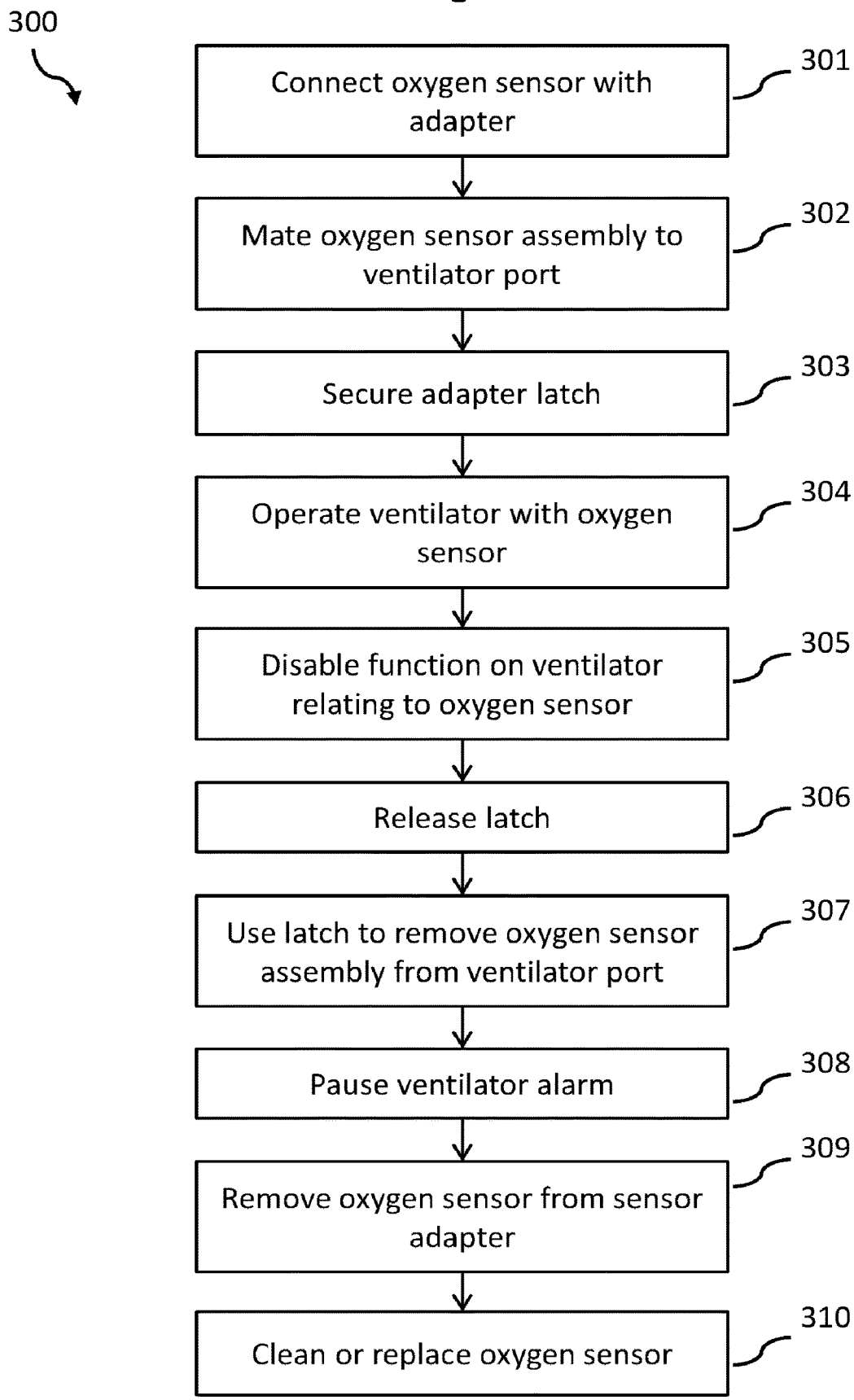
FIG. 5 illustrates a method for installing and removing an oxygen sensor on a ventilator, according to an embodiment of the present disclosure.

FIG. 5 illustrates a method 300 for replacing an oxygen sensor in a medical ventilator, according to an embodiment of the present disclosure. The method includes connecting an oxygen sensor with an adapter, at 301. The combined components form the oxygen sensor assembly (such as assembly 210 in FIG. 2). This first step is omitted where the oxygen sensor and adapter are integrated together in one piece. The method 300 includes mating the oxygen sensor assembly to the ventilator port, at 302. In an embodiment, mating the oxygen sensor assembly to the port includes sliding, pushing, or threading the assembly into the port, forming a seal between the assembly and the port, and engaging the valve (such as valve 226 in previous figures) to open the valve, as described in further detail above. In an embodiment, this step also includes electrically connecting the oxygen sensor to the ventilator. The oxygen sensor may include a separate wired electrical connector that plugs into a corresponding electrical port on the ventilator, to enable the oxygen sensor and ventilator to communicate. After mating the oxygen sensor assembly to the port, the method includes securing the adapter latch at 303. The latch retains the sensor assembly to the port and confirms that the sensor assembly has been installed to the correct depth. In an embodiment, the latch is secured after the oxygen sensor assembly is inserted into the port, so that the latch can engage the ventilator (such as the clip 270) when the latch is secured. With the oxygen sensor installed, the method includes operating the ventilator with the oxygen sensor, at 304. The ventilator may continue to operate with the oxygen sensor for several months without any need to remove, replace, or inspect the sensor. When functioning properly, the oxygen sensor samples the air flowing to the patient circuit, measures the oxygen concentration in the air, and provides that measurement to the ventilator (such as to the processor 116) so the ventilator can confirm that the desired concentration is being provided.

At some point, the oxygen sensor may become exhausted, clogged, or broken. A user may replace or clean the sensor on a set schedule, such as every few months, or may wait for the ventilator to indicate that the sensor is not functioning correctly. The method 300 optionally includes disabling a function on the ventilator relating to the oxygen sensor, such as an alarm, warning message, or oxygen sensor functionality, at 305. The user may accomplish this through the user interface. This step is optional. The method 300 includes removing the oxygen sensor assembly by first releasing the latch at 306, and then using the latch to remove the oxygen sensor assembly from the port, at 307. This may be done as described above with references to FIGS. 4A-C. When the oxygen sensor assembly is removed, the ventilator may activate an alarm or warning, if not earlier paused or disabled. The method includes pausing or disabling the ventilator alarm at 308. This is optional, and may not be relevant if the ventilator does not activate an alarm. The method includes removing the oxygen sensor from the sensor adapter, at 309, if the two components are separate. Optionally, the method includes cleaning or replacing the oxygen sensor at 310, and from there the method may be repeated.

The method outlined in FIG. 5 may vary in other embodiments. For example, in some embodiments, the oxygen sensor itself can be directly inserted into the ventilator to interact with the port and the port valve, without a sensor adapter. As another example, the valve may be operated independently of the sensor or sensor assembly, such that the valve is separately actuated into an open or closed position, independently of removal or insertion of the valve. In this case, the valve is not automatically opened or closed when the sensor or sensor assembly is inserted or removed, but can be separately opened or closed via its own actuator or switch. An oxygen sensor can be inserted, then the valve opened, and later the valve can be closed, and then the sensor removed.

Though a spring-biased plunger valve is shown in the figures, it should be understood that other types of valves may be suitable for closing the oxygen sensor port, in other embodiments. For example, other suitable valves include flapper valves, duck valves, umbrella valves, gate valves, and butterfly valves. In other embodiments, the valve may be operated by a user, such as by a turn handle, or by a solenoid or other actuator. An actuator can be operated by a user, or automatically activated by a switch or sensor that is triggered when the oxygen sensor is removed.

Additionally, while the oxygen sensor 222 and the sensor adapter 224 are shown in the figures as separate components, in another embodiment, the two are integrated together into one piece. The housing of the adapter may include the features that interact with the port 216, such as a seal 256, front face 244, and wing 272. The sensor itself can then be inserted into the port, with the front face of the sensor contacting the valve to open it, and the seal contacting the port to prevent leaks. The wing, or a similar feature formed on the sensor body itself, can interact with the clip 270 to retain the sensor to the port. A movable latch such as latch 254 may be integrated with the body or housing of the sensor itself. In such an embodiment, the sensor is not removed from a separate adapter housing, and there is no need to provide an engagement or seal (such as threads) between the sensor and adapter.

Although the present invention has been described and illustrated in respect to exemplary embodiments, it is to be understood that it is not to be so limited, since changes and modifications may be made therein which are within the full intended scope of this invention as hereinafter claimed.

What is claimed is:

1. A method for replacing an oxygen sensor on a medical ventilator, comprising:
    inserting an oxygen sensor into a cavity of a sensor adapter to form an oxygen sensor assembly; mating the oxygen sensor assembly to a port of a medical ventilator by rotating, about a hinge, a latch of the sensor adapter to secure the oxygen sensor in the sensor adapter and the sensor adapter in the port, the port comprising a valve biased to close the port;
    wherein said latch is disposed behind the oxygen sensor;
    operating the medical ventilator with the oxygen sensor;
    and removing the oxygen sensor assembly from the port, wherein the step of mating the oxygen sensor assembly to the port comprises opening the valve, and wherein the step removing the oxygen sensor assembly from the port comprises closing the valve;
    and removing the oxygen sensor from the sensor adapter.

2. The method of claim 1, further comprising disabling a setting of the medical ventilator relating to the oxygen sensor prior to removing the oxygen sensor assembly from the port.

3. The method of claim 1, further comprising pausing an alarm or alert after removing the oxygen sensor assembly from the port.

4. The method of claim 1, wherein mating the oxygen sensor assembly to the port comprises automatically opening the valve, and wherein removing the oxygen sensor assembly from the port comprises automatically closing the valve.

5. The method of claim 4, wherein mating the oxygen sensor assembly to the port comprises making physical contact between the oxygen sensor assembly and the valve to open the valve.

6. The method of claim 4, wherein mating the oxygen sensor assembly to the port comprises triggering an actuator that opens the valve.

7. A method for replacing an oxygen sensor on a medical ventilator, comprising:
    inserting the oxygen sensor into a cavity of a sensor adapter;
    inserting the sensor adapter into a port of a manifold of a medical ventilator;
    rotating, about a hinge, a latch of the sensor adapter to secure the oxygen sensor in the sensor adapter and the sensor adapter in the port; wherein said latch is disposed behind the oxygen sensor;
    and opening a valve of the port to allow gases from the medical ventilator to reach the oxygen sensor.

8. The method of claim 7, wherein securing the sensor adapter in the port causes the opening of the valve.

9. The method of claim 7, wherein rotating the latch causes a clip of the manifold to engage with a wing of the latch.

10. The method of claim 9, further comprising:
after securing the sensor adapter in the port, again rotating the latch to release the wing from the clip; and
removing the sensor adapter from the port.

11. The method of claim 7, further comprising closing a rear door, of the manifold, behind the latch.

12. The method of claim 7, wherein rotating the latch comprises mating a detent of a foot of the latch with a groove of the sensor adapter.

13. The method of claim 7, wherein rotating the latch includes applying force to a grip of the latch located opposite the hinge about which the latch rotates.

\* \* \* \* \*